(12) United States Patent
Archer et al.

(10) Patent No.: US 8,133,717 B2
(45) Date of Patent: Mar. 13, 2012

(54) STEREOINVERSION OF AMINO ACIDS IN A SINGLE REACTOR

(75) Inventors: Ian Victor James Archer, East Lothian (GB); Ian Fotheringham, Edinburgh (GB); Rueben Carr, Edinburgh (GB); Susan Alison Arnold, Edinburgh (GB)

(73) Assignee: Richmond Chemical Corporation, Oak Brook, IL (US)

( * ) Notice: Subject to any disclaimer, the term of this patent is extended or adjusted under 35 U.S.C. 154(b) by 978 days.

(21) Appl. No.: 11/963,737

(22) Filed: Dec. 21, 2007

(65) Prior Publication Data

US 2008/0153137 A1    Jun. 26, 2008

Related U.S. Application Data

(60) Provisional application No. 60/876,756, filed on Dec. 22, 2006.

(51) Int. Cl.
*C12P 41/00* (2006.01)

(52) U.S. Cl. ......................................................... 435/280

(58) Field of Classification Search .................. None
See application file for complete search history.

(56) References Cited

U.S. PATENT DOCUMENTS

| 5,077,217 | A | 12/1991 | Matson et al. ................. 435/280 |
| 5,728,555 | A | 3/1998 | Fotheringham et al. ....... 435/106 |
| 6,365,380 | B2 | 4/2002 | Liu et al. ......................... 435/106 |
| 2006/0063238 | A1 | 3/2006 | Hummel et al. ............... 435/106 |

FOREIGN PATENT DOCUMENTS

| WO | WO9842643 | 10/1998 |
| WO | WO 00-18708 | 4/2000 |
| WO | WO 01-12574 | 2/2001 |
| WO | WO 02-44111 | 6/2002 |
| WO | WO 03-080855 | 10/2003 |

OTHER PUBLICATIONS

Cooper et al., "Synthesis and Properties of the alpha-Keto Acids", Chemical Reviews 83 (3) : 321-358 (1983).*
Alexandre et al., "Amine-boranes: effective reducing agents for the deracemisation of DL-amino acids using L-amino acid oxidase from Proteus myxofaciens" Tetrahedron Letters 43 : 707-710 (2002).*
Alonso, et al., "Engineering the D-Amino Acid Oxidase from Trigonopsis Variabilis to Facilitate It Overproduction in *Escherichia coli* and Its Downstream Processing by Tailor-Made Metal Chelate Supports", Enzyme and Microbial Technology, vol. 28, pp. 88-95, (1999).
Caligiuri, et al., "Enzymatic Conversion of Unnatural Amino Acids by Yeast D-Amino Acid Oxidase", Advanced Synthesis & Catalysis, vol. 348, pp. 2183-2190, (2006).
Fotheringham, et al., "Preparative Deracemization of Unnatural Amino Acids", Biochemical Society Transactions, vol. 34, No. 2, pp. 287-290, (2006).
Geueke, et al., "A New Bacterial L-Amino Acid Oxidase with a Broad Substrate Specificity: Purification and Characterization", Enzyme and Microbial Technology, vol. 31, pp. 77-87, (2002).
Kim, et al., "Dynamic Kinetic Resolutions and Asymmetric Transformation Enzymes Coupled with Metal Catalysis", Current Opinions in Biotechnology, vol. 13, pp. 578-587, (2002).
Martin-Matute, et al., "Highly Compatible Metal and Enzyme Catalysts for Efficient Dynamic Kinetic Resolution of Alcohols at Ambient Temperature", Angewandte Chemie International Edition, vol. 43, pp. 6535-6539, (2004).
Ogo, et al., "Ph-Dependent Chemoselective Synthesis of Alpha-Amino Acids. Reductive Amination of Alpha-Keto Acids with Ammonia Catalyzed by Acid-Stable Iridium Hydride Complexes in Water", Journal of the American Chemical Society, vol. 126, pp. 3020-3021, (2004).
Pamies, et al., "Combined Metal Catalysis and Biocatalysis for an Efficient Deracemization Process", Current Opinion in Biotechnology, vol. 14, pp. 407-413, (2003).
Syrris, "Flow-vs-Batch", Syrris: Batch chemistry or Flow chemistry, http://www.syrris.com/Flow-vs-Batch.aspx, (Dec. 13, 2006).
Turner, et al., "Controlling Chirality", Current Opinions in Biotechnology, vol. 14, pp. 401-406, (2003).
Turner, et al., "Novel Biocatalyst Technology for the Preparation of the Chiral Amines", Innovations in Pharmaceutical Technology, pp. 114-122, (Jun. 2004), www.iptonline.com/articles/public/Ingenza1.pdf, (Jul. 20, 2004).
Uematsu, et al., "Asymmetric Transfer Hydrogenation of Imines", Journal of the American Chemical Society, vol. 118, pp. 4916-4917, (1996).
Wikipedia, "Batch v Flow Basics", http://en.wikipedia.org/wiki/Flow_chemistry (Dec. 13, 2006).
Worthington, "Worthington D-Amino Acid Oxidase Manual Page", D-aa Oxidase Information, http://www.worthington-biochem.com/DAOFF/default.html, (Dec. 22, 2006).
Worthington, "Worthington L-Amino Acid Oxidase Manual Page", L-aa Oxidase Information, http://www.worthington-biochem.com/LAO/default.html, (Dec. 22, 2006).

* cited by examiner

*Primary Examiner* — Sandra Saucier
(74) *Attorney, Agent, or Firm* — Donald J. Silvert; Rosenbaum & Silvert, P.C.

(57) ABSTRACT

A process is described to prepare a single enantiomer of an amino acid from its opposite enantiomer or from a racemic mixture, using an oxidase biocatalyst and a supported metal catalyst in separate, sequential reactions in water. The process can be operated in batch or continuous mode.

24 Claims, 1 Drawing Sheet

STEREOINVERSION OF AMINO ACIDS IN A SINGLE REACTOR

CROSS REFERENCE TO RELATED APPLICATIONS

This application claims the benefit of priority to U.S. Patent Application Ser. No. 60/876,756, filed Dec. 22, 2006.

REFERENCE REGARDING FEDERALLY SPONSORED RESEARCH OR DEVELOPMENT

Not applicable

SEQUENCE LISTING

Not applicable

BACKGROUND OF THE INVENTION

1. Field of the Invention

The present invention relates to the manufacture of enantiomerically-enriched preparations of amino acids and materials useful therefor. In particular, the present invention relates to an efficient industrial method to prepare natural or unnatural amino acids in high yield and high enantiomeric purity by stereoinversion of the opposite enantiomer using sequential reactions of biocatalytic oxidation and chemocatalytic reductive amination.

2. Description of the Background of the Invention

Amino acids typically exist in two mirror-image forms, known as "optical isomers" or "enantiomers". This phenomenon is due to the asymmetric nature of these molecules, which underlies their molecular configurations referred to as left- and right-handed (chiral) forms. These forms are conventionally designated dextro (D) and levo (L) which display the optical property of shifting polarized light to either the right or the left as the light passes through such molecules. Both nature and industry use amino acids of one or the other chiral form, as appropriate, for given applications; hence, users of amino acids experience increased efficiency of use to the extent that the amino acids employed are optically-pure or -enriched for D- or L-amino acids, as appropriate. In industry, amino acid preparations are used for production of pharmaceutical, agrochemical, and fine chemical products.

To meet the industrial demand for these compounds, many methods have been described and developed to prepare amino acids with a high degree of optical purity. These methods include the physical separation or resolution of enantiomeric pairs using chromatographic or crystallization methods, biocatalytic resolution of enantiomers using enzymes, asymmetric synthesis of single enantiomers using chemical and/or biological catalysts, fermentation methods using engineered microbes, or selective stereoinversion methods. This last method combines a stereoselective enzyme (a biocatalyst) that forms an imine or keto acid intermediate and a non-selective metal catalyst (a chemocatalyst) that facilitates reduction of the intermediate species into a racemic amino acid mixture. Sequentially repeating this process results in a high degree of stereo-specific purity.

While each of the aforementioned approaches has been successful in specific instances, each has been limited by inherently low efficiency and/or narrow applicability to the broad family of amino acids required by industry. For example, fermentation methods are limited to the production of natural amino acids, whereas most of the amino acids required for pharmaceutical and agrochemical applications are unnatural. Resolution methods are limited in almost all cases to a maximum product yield of 50%, thereby incurring costs and generating waste in the forms of solvents and unreacted by-products at a minimum. Asymmetric synthesis of amino acids using chemical and biological catalysts is limited by many factors, including the narrow substrate ranges of the chemo- and biocatalysts employed in the process, limited access to starting materials, and greater expenses related to such starting materials.

Selective stereoinversion methods as currently practiced combine the biocatalyst and the chemocatalyst in a "one-pot" reaction. Accordingly, both the biocatalyzed oxidation and the chemocatalyzed reduction reactions operate under the same conditions. In practice, this limits the (potentially more robust) reduction reaction because it must be carried out under milder conditions amenable to the more sensitive biocatalytic reaction, such as a relatively moderate pH and a relatively low temperature. As a consequence, the activity of the metal catalyst is low, necessitating high catalyst usage to achieve reasonable rates of conversion. Neither does the oxidase enzyme operate optimally under current methodologies due to the compromise to use higher than optimal temperature conditions, for example, in order to lessen the detrimental impact on the metal catalyst activity under the biocatalyst-driven milder conditions.

Further drawbacks of the selective stereoinversion method as currently practiced includes the inhibitory effects of the biocatalyst and chemocatalyst on each other. The biocatalyst binds efficiently to the metal catalyst, whereupon both catalysts deactivate. Yet another drawback relates to safety in operating the selective stereoinversion method as a "one-pot" process. Oxygen gas is a requirement for the biocatalytic oxidation reaction. The following reduction reaction uses hydrogen gas as a co-substrate or produces some hydrogen gas as a byproducts of transfer hydrogenation. Therefore, both oxygen gas and hydrogen gas are present simultaneously in the same reaction vessel. At large scale, the possibility of a catastrophic explosion is high.

The current disclosure relates to a significant and surprising improvement of the selective stereoinversion method. This improved method, as disclosed below, overcomes the limitations of the previously described process by (i) avoiding the compromise conditions for the oxidation and reduction reactions, (ii) preventing the inhibition of both catalysts, and (iii) eliminating the requirement for simultaneous oxidizing and reducing conditions in the same reaction vessel. The process described herein also achieves a superior product yield. Additionally, as both reactions may be run under optimal conditions, the volumetric productivity (space-time yield) is significantly improved. Thus, the present invention greatly enhances the efficiency, scope, and safety of this process.

SUMMARY OF THE INVENTION

The current disclosure describes a process of stereoinversion to prepare a single enantiomer of an amino acid from its opposite enantiomer, from a racemic mixture, or from one or more amino acid intermediates using an oxidase biocatalyst and a chemical reductant in separate reactions. The enantioselective biocatalyst converts the undesired enantiomer of the amino acid to its corresponding keto acid or imine, which is subsequently converted by the metal catalyst to the original enantiomer and the desired opposite enantiomer in equal proportions. The chemical reduction employs a chemical reducing agent or hetero- or homogeneous metal catalyst in combination with hydrogen gas or catalytic transfer hydrogenation. Several cycles of this process are carried out to yield the desired optically pure single enantiomer in high yield.

In one aspect, a process to stereoinvert a first enantiomer into a second enantiomer in a reactor includes the steps of (a) combining the first enantiomer, oxygen, and a first catalyst, thereby resulting in an intermediate, and (b) combining the intermediate, a second catalyst, a reductant, and an amine source, thereby resulting in the second enantiomer. Step (a) and step (b) take place at different times.

In another aspect, a process to stereoinvert a first enantiomer into a second enantiomer in a reactor that includes a first surface and a second surface includes the steps of (a) combining the first enantiomer, oxygen, and a first catalyst that is in contact with the first surface, thereby resulting in an intermediate, and (b) combining the intermediate, a second catalyst that is in contact with the second surface, a reductant, and an amine source, thereby resulting in the second enantiomer. The first catalyst and the second catalyst are prevented from contacting each other.

In another aspect, a process to stereoinvert a first enantiomer into a second enantiomer in a reactor that includes a first surface and a second surface includes the steps of (a) combining the first enantiomer, oxygen, and a first catalyst that is in contact with the first surface, thereby resulting in an intermediate, and (b) combining the intermediate, a second catalyst that is in contact with the second surface, a reductant, and an amine source, thereby resulting in the second enantiomer. Preferably, step (a) or step (b) is performed first. More preferably, step (a) is complete before step (b) begins. In another embodiment of the invention, step (a) and step (b) are performed at or near different sites of reaction.

In a further aspect, a process to stereoinvert a first enantiomer into a second enantiomer in a reactor that includes a first surface and a second surface includes the steps of (a) combining the first enantiomer, oxygen, and a first catalyst that is in contact with the first surface, thereby resulting in at least one of a keto acid intermediate or an imine intermediate, and (b) combining the at least one of a keto acid intermediate or an imine intermediate, a second catalyst that is in contact with the second surface, a reductant, and an amine source, thereby resulting in the second enantiomer. The first catalyst and the second catalyst are preferably prevented from contacting each other. Preferably, the first catalyst is an enantioselective amino acid oxidase that is specific for D-amino acids or L-amino acids. In a preferred embodiment, the second catalyst is a metal catalyst that includes palladium on carbon, the reductant includes hydrogen gas, and the amine source is ammonia or an ammonium salt.

DETAILED DESCRIPTION

Figure 1:
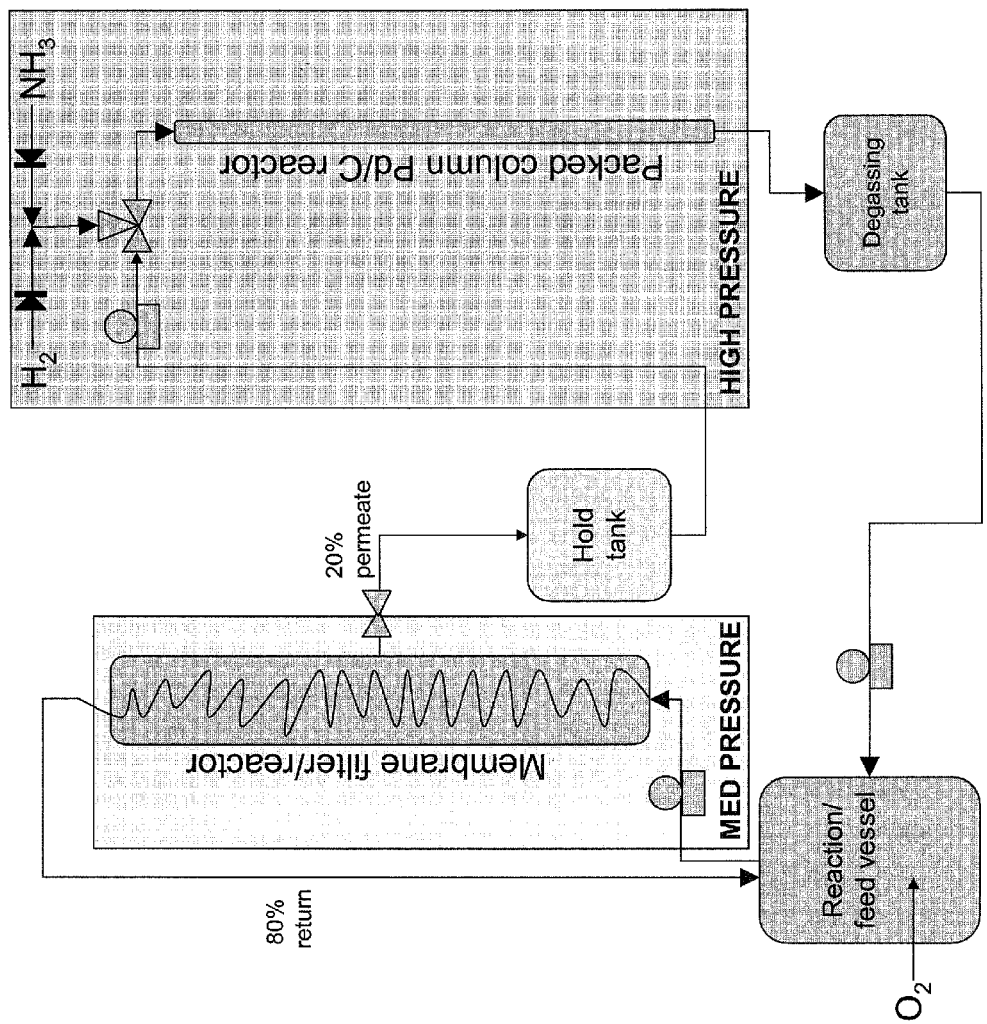
FIG. 1 is one reactor system that may be usefully employed in the present invention.

The present invention describes a process to prepare one enantiomer of an amino acid from its opposite enantiomer (stereoinversion). This process takes place in the context of a solution that (i) is enriched for the one enantiomer, even to the point of "purity," (ii) includes concentrations of both the one enantiomer and its opposite enantiomer, i.e., a racemic mixture, or (iii) includes an enantiomerically-enriched or a racemic mixture, together with chemical species or other molecules that may or may not have chiral properties. Because even the process as used on an initially "pure" enantiomeric preparation will include steps where the subject-amino acid solution contains a racemic mixture, the present invention is described herein interchangeably as a "deracemization" or "stereoinversion" method or process.

In particular, the present invention relates to a new method of deracemization whereby a biocatalyzed oxidation and a chemocatalyzed reduction reaction take place separately and sequentially. The oxidation and reduction steps take place at differing times in sequence; the location of the separate steps can be different or the same so long as the catalysts employed for the two steps do not contact one another. In one step, an enantioselective biocatalyst converts the undesired enantiomer of the amino acid to its corresponding keto acid, which is subsequently converted by a metal catalyst to the original enantiomer and the desired opposite enantiomer in equal proportions. The chemical reduction employs a chemocatalyst, which is also referred to here in as a chemical reducing agent. The chemocatalyst is preferably a hetero- or homogeneous metal catalyst; more preferably, the chemocatalyst is a heterogeneous metal catalyst, which is further described below. The chemocatalyst is employed, preferably, in combination with hydrogen gas or a suitable chemical species for catalytic transfer hydrogenation. This sequential process may be repeated to yield the desired optically-enriched enantiomer in the desired end concentration. A desired end concentration of the desired enantiomer relative to the total amino acid content can be, for example, and without limitation intended, about 40%, about 50%, or about 70%. Preferably, the end concentration of the desired enantiomer that results from using the process is about 80%, more preferably, about 90%, yet more preferably, about 95%, even more preferably, about 98%, and most preferably, about 99%. In the context of the present invention, a "pure" preparation of an amino acid of a given enantiomer, as determined by enantiomeric excess, is at least 97% pure, preferably at least 98% pure, more preferably, at least 99% pure, and most preferably, at least 99.9% pure.

The present process offers several advantages over previously described deracemization processes. Primarily, it can be used to deracemize substrates that do not form a stable imine intermediate of the oxidation step as is required for earlier processes, while at the same time accommodating imines as substrates for the process. The present process, instead, can proceed for those substrates that accumulate a keto acid intermediate upon oxidation. Secondly, the present process includes an option for operation of the oxidation and reduction steps at different physical locations, which are referred to herein as "sites of reaction." For example, a site of reaction can be in a vessel and a second site of reaction can be in a second vessel; alternatively, or in addition, a site of reaction can be in one region of a conduit and a second site of reaction can be in a second region of the conduit; yet a further alternative, one site of reaction can be in a vessel and a second site of reaction can be in a region of a conduit, where the conduit is preferably in fluid communication with the vessel. Other configurations of locations of sites of reaction are contemplated as well, such as, for example, where two or more sites of reaction are included within the same vessel or tube, and where one or all of the sites of reaction are removable from the reactor. In another embodiment of the present invention, a site of reaction and a second site of reaction can be located in the same vessel or conduit, but not at the same point in time, thereby accommodating variation of physical and chemical conditions appropriate to differing reactions, as further described below.

Inclusion of separate surfaces at which sites of reactions are respectively proximate allows the method of the present invention to include two or more reactions that occur under differing optimized conditions to occur at different sites and/or at different times. This feature of the present invention substantially lessens one likely source of fire and explosion hazards in the prior method. As more fully described above, a foreseeable hazard of the prior art process relates to the requirement for oxygen and hydrogen gases to be present at or about the same site of reaction, such as, without limitation, in the same vessel or conduit at the same time. Thirdly, the separate operation of the biocatalyst and the chemocatalyst achieves greatly accelerated reaction rates and increased productivity by (i) eliminating strong inhibitory effects exerted by the two catalysts upon each other and (ii) allowing optimal conditions to be employed at each step.

The starting material for this process can be an amino acid, either as the undesired enantiomer or a mixture of the two enantiomers in any ratio. Alternatively, the starting material can be the intermediates of the process, i.e., imines or keto acids corresponding to amino acids of interest. In yet another embodiment, the starting material can contain a combination of amino acid and intermediates. In yet a further embodiment, any suitable precursor can be processed into the desired enantiomeric end product by means of process described herein. The suitability of a precursor is determined by the ability of the precursor to be chemically altered by the oxidation and reductive chemistries disclosed herein, resulting in an amino acid of interest.

As used in this document, the term "vessel" means any container that holds a fluid, preferably a reaction mixture or a component for a reaction mixture or the results of a reaction. The vessel or vessels used in the context of the present invention are preferably in fluid communication with each other and/or with and by conduits usefully employed in the reactor systems described herein and/or known in the art.

Similarly, it is also contemplated herein for semi-permanent and/or permanent immobilization of chemocatalyst on a surface using standard methods known in the art. The surface can be part of a structure; the surface can be metal or ceramic or another material appropriate to this purpose.

The process presented herein can be described as "stereo-inversion," in particular when the starting material is a single enantiomer of an amino acid, or "deracemization" when the starting material includes a racemic mixture of both enantiomers. Irrespective of the nature of the starting material, an undesired enantiomer may be converted to the opposite enantiomer via the process of the present invention. Moreover, the process of the present invention anticipates starting materials including keto acid and imine intermediate, as well. These intermediates may be commercially obtained, and/or generated by oxidizing an undesired enantiomer of an amino acid. Preferably, starting materials as well as products of the process described herein may be any amino acid of the general structure RCH(NH2)COOH, where R can be a range of alkyls or aryls that may be substituted, cyclized, or otherwise altered so long as the R group is compatible with the core structure of the amino acid and non-inhibitive of the general process described herein.

The biocatalyst used in the context of the present invention is preferably an amino acid oxidase. For example, an L-amino acid oxidase ("LAO") biocatalyst is specific for an L-amino acid and thus enables enrichment of the D-form of the amino acid in question. Conversely, use of a D-amino acid oxidase ("DAO") biocatalyst results in enrichment of the L-amino acid. Amino acid oxidase biocatalysts with enantioselectivity for either L- or D-amino acids are well-known among skilled artisans and are available from commercial sources. See, e.g., Worthington Biochemical Corporation, Lakewood, N.J., or Sigma-Aldrich, Inc., St. Louis, Mo., either of which sells DAO from porcine kidney and LAO from snake venom. Alternatively, LAO or DAO may be generated using recombinant technology and/or isolated using standard methods of protein purification technology. For example, amino acid oxidase biocatalysts can be isolated from natural sources, including animals and microorganisms, among others. Examples of preferred amino acid oxidases are described in U.S. Pat. Nos. 5,728,555 and 6,365,380, and in Caligiuri et al., ADV. SYNTH. CATAL. 348:2183-2190 (2006) and Geueke and Hummel, ENZYME AND MICROBIAL TECHNOLOGY 31:77-87 (2002), which are hereby incorporated herein in their respective entireties with respect to methods for generating DAO or LAO. A more preferred amino acid oxidase is derived from a yeast. In particular, with respect to a D-amino acid oxidase, a yet more preferred amino acid oxidase is that derived from *Trigonopsis variabilis, Rhodoturula graminis*, or *Streptomyces ceolicolor*. With respect to an L-amino acid oxidase, a yet more preferred amino acid oxidase is that derived from *Rhodococcus opacus* or *Synechococcus* sp.

Genes encoding amino acid oxidase biocatalysts are well described and may be identified using bioinformatics as known in the art. For example, one can parse genomic and/or proteomic data available to the public with known search algorithms for conserved DNA sequences and/or protein domains. Examples of databases and algorithms usefully employed for this purpose may be found at the National Center for Biotechnology Information (NCBI—http://www.ncbi.nlm.nih.gov/) and at UniProt (Universal Protein Resource—http://www.expasy.uniprot.org/). In addition, amino acid oxidase biocatalysts usefully employed in the context of the present invention may be identified using biological screening methods and isolated using methods known in the art, such as polymerase chain reaction (PCR), hybridization, and other techniques of molecular biology and/or nucleic acid chemistry. Genes encoding amino acid oxidases may be introduced respectively into host microorganisms within a suitable plasmid or other vector. A suitable plasmid or other vector may be selected based on the requirements or proclivities of the host organism into which the gene of interest is to be cloned. Suitability may also relate to appropriate genetic elements included therewith for optimizing selection of recombinant clones and generation of gene products therein. Appropriate regulatory elements can be important in these selections, are well-known in the art, and are described in various laboratory Guides, such as, for example, *Molecular Cloning: A Laboratory Manual* (Sambrook et al. Cold Spring Harbor Laboratory Press; 2nd edition, December, 1989). Suitable vectors include, for example, those available from Novagen, a subsidiary of EMD Biosciences Inc. (San Diego, Calif.). The amino acid oxidase biocatalysts may subsequently be expressed at high levels via well-characterized, heterologous regulatory regions encoded in the vector. In this way, suitable biocatalysts may be prepared by fermentation of recombinant microorganisms including, but not limited to *Escherichia* (e.g., *E. coli*), *Bacillus, Pseudomonas*, and yeast (e.g., *T. variabilis*) species. Amino acid oxidase biocatalysts usefully employed in the context of the present invention include wild type and/or variant genes and/or cDNAs and/or ESTs generated by random and/or rational genetic mutations isolated from the biosphere or generated de novo. A preferred source for genetic material is any of the organisms identified above as preferred sources of amino acid oxidases, in addition to the American Type Culture Collection or the NRRL culture collection. Further, amino acid oxidase biocatalysts contemplated for use herein include those adapted for extremophilic conditions, such as, for example, those that may be isolated from thermophilic, barophilic, psychrophilic, halophilic, basophilic, or acidophilic organisms, to mention specific examples without limitation.

D- and L-amino acid oxidase biocatalysts are FAD-dependent enzymes. They may be employed in the context of the present invention in a variety of preparations and degrees of purity, including, for example, within whole cells, as purified enzymes, and/or as partially-purified cell fractions. Methods contemplated herein for their application include whole cell immobilization in a suitable matrix, such as, for example, agarose or polyacrylamide gels. Other suitable whole and/or partial cell immobilization approaches are equally considered within the context of the present disclosure. Suitable methods for preparing partially purified cell fractions include simple cell disruption using a French Pressure Cell or other mechanical methods known in the art to disrupt cells and cellular membranes such as sonication, among others known in the art. Further, chemical approaches to isolating any suitable biocatalyst are contemplated herein, including, for example, ammonium sulfate precipitation and other approaches known in the art. Various methods for biocatalyst purification are contemplated herein, including, but not limited to, affinity chromatography, size exclusion assays, dialysis, and the like.

In a preferred embodiment, the D-amino acid oxidase biocatalyst may be isolated from recombinant *E. coli* grown to a high biomass using standard fed-batch fermentation protocols. DAO used in the context of the present invention is preferably an enriched, highly active, and highly stable ammonium sulfate fraction of disrupted recombinant *E. coli* designed and cultured to generate DAO. The disrupted bacteria are then processed using standard methods to provide a partial purification of DAO.

Further contemplated herein are suitable methods for semi-permanent and/or permanent immobilization of functional proteins on a surface by means of, for example, physisorption and chemisorption. The surface can be part of a structure, as further described below. Alternatively, the surface can be multi-faceted or discontinuous, as in a grid or a matrix. In a straight-forward manner, the surface preferably serves as a support material for a catalyst. Accordingly, in one embodiment, a functional protein, such as a biocatalyst, may be immobilized using self-assembled monolayers, as is known in the art.

In a preferred embodiment, a process is provided to stereoinvert a first enantiomer into a second enantiomer of an amino acid. The amino acid is a D- or L-enantiomer; in one embodiment, the process is applied on a racemic mixture of an amino acid. In another embodiment, the process is applied on a mixture of different amino acids, which amino acids are respectively D- or L-enantiomers or mixtures thereof. In a further embodiment, the process is applied on a mixture of imine and/or keto acid precursors of amino acids of interest in that a reduction or a reduction amination reaction therewith generates the amino acids of interest. In yet another embodiment, the present invention of stereoinverting enantiomers of one or more amino acids takes place in the presence of non-amino acid chemical species, including other macromolecules. While the present process is directed toward the purification of one enantiomer over another, additional uses are contemplated herein including, for example, applying the process to an unknown mixture in order to determine the contents thereof.

In the process, the first enantiomer of an amino acid is stereoinverted into the second enantiomer thereof in a reactor that preferably includes a first surface and a second surface. The first surface and the second surface are preferably associated with a first catalyst and a second catalyst, respectively. The first surface is further described below with respect to the first catalyst. The second surface is further described below, as well, in the context of the second catalyst.

The process of the present invention preferably takes place in a reactor that includes one or more sites of reaction. A site of reaction is a defined region of the reactor (also referred to herein as a reaction apparatus) where a reaction takes place or is designed to take place. For example, a site or sites of reaction can be associated with one or more reaction vessels or conduits. Such sites associated with a vessel or a conduit can be an interior surface of the vessel or conduit, or a location that is proximate thereto. Alternatively, such sites can be on or proximate to a surface that is removably inserted into the vessel or conduit. In one embodiment, such vessels are designed for batch reactions and/or elongated reactions in the context of a continuous, semi-continuous, and/or saltatory flow apparatus (relative to the residence time of a molecule in the conduit portions thereof). As implicated above, a site of reaction can also be situated in a continuous flow reactor at a location within and/or on an interior surface of a conduit, for example. A site of reaction can be included in a continuous flow reactor in a vessel, as well, where the vessel is designed to hold a fluid for an extended period in order that it be associated with a site of reaction for a period longer than may be accommodated readily within the conduit portions thereof. Preferably, the sites of reaction are associated with the first catalyst and the second catalyst, respectively, as further set forth below.

The term "conduit" as used herein refers to a means for coursing a fluid in or about a reactor. A conduit can have any shape that includes a hollow interior that further includes an inlet at one end and an outlet at another end. The conduit can follow any path between inlet and outlet points. In one embodiment, the conduit follows a direct path that is as close to the line formed by the points of inlet and outlet as permitted by other parts and requirements of the reactor. In another embodiment, the conduit is coiled or otherwise caused to have additional surface area exposed to a heat exchanger or the like in order to affect the temperature conditions of the fluid.

The amino acid that is subject to the present process may be any that includes at least one asymmetric carbon and therefore is chiral in nature. The amino acid can be one synthesized within the biosphere; alternatively, the amino acid subject to the present invention can be unnatural, i.e., not found in the biosphere apart from an organism that was genetically altered to produce the otherwise unnatural amino acid. Generically, the amino acids subject to the present stereoinverting method can be D-amino acids or L-amino acids or mixtures thereof.

The site of reaction is preferably located within a reactor. The reactor can be designed for batch or flow-through (fixed bed) processing. Irrespective of the design, the site of reaction is itself at minimum a point or surface at or near which a step of the process is catalyzed by, in one embodiment, a biocatalyst and/or a chemocatalyst; in a preferred embodiment, the biocatalyst or the chemocatalyst are attached to a surface. In another preferred embodiment, both biocatalyst and chemocatalyst are attached to surfaces. In yet another preferred embodiment, the biocatalyst and/or chemocatalyst are free floating. The surface can be located in or on a vessel or in or on a conduit, or in or on both locations. The surface can be attached to the reaction apparatus; alternatively, the surface can be attached to or contained by a structure that itself is inserted into and removed from the reaction structure at appropriate time points in the process. The structure is preferably a catalyst cage or a catalyst basket as are known in the art. Additional suitable structures include, for example, any structure upon and/or within which a biocatalyst and/or a metal catalyst can be permanently or semi-permanently affixed, such as, a tube, a cylinder, a conduit, a hose, a microfluidic channel, a capillary space, a flat surface, a hard surface, a soft surface, a plate, a wire, a rod, and the like. The surface described in this paragraph can be the first surface that is preferably associated with the first catalyst. In addition or in the alternative, the surface described in this paragraph can be the second surface that is preferably associated with the second catalyst. Either the first surface or the second surface can be associated with the aforementioned structure. Preferably, the first catalyst and the second catalyst are associated with separate structures, albeit not necessarily so long as the two catalysts are restrained from making contact with one another.

In particular, the reactor usefully employed in the context of the present invention preferably includes one or a combination of reactors selected from the group consisting of a stirred tank reactor, a fermentation vessel, a hollow fiber membrane bioreactor, an oscillatory baffled reactor, a fixed bed reactor, and a counter current chromatographic reactor. More preferably, the reaction apparatus used in the context of the present invention includes one or more batch reactors, and/or one or more bed reactors. Yet more preferably, the reaction apparatus used in the context of the present invention is a stirred tank reactor (preferably for oxidation), a membrane reactor, and a continuous fixed bed reactor (preferably for reduction). The process of the present invention, that is, to stereoinvert a first enantiomer into a second enantiomer in a reactor, preferably includes step (a) of combining the first enantiomer with oxygen and a first catalyst, thereby resulting in an intermediate. Preferably, the intermediate is an imine or a keto acid. The first enantiomer, as contemplated in the present invention, may be that of a natural amino acid, or an unnatural amino acid, among others. Specific examples of the foregoing intermediates are well known to skilled artisans. In one embodiment, the reactor includes a first surface and a second surface, wherein the first catalyst is in contact with the first surface.

Any source of oxygen can be employed in the method of the present invention, including, for example, ambient air and/or oxygen gas having varying degrees of purity. Other sources for oxygen known in the art are further contemplated for use herein.

The first catalyst is preferably a catalyst that performs one or more steps in the conversion of a first enantiomer of an amino acid into a second enantiomer of the same amino acid. For example, a D-amino acid can be converted into an L-amino acid, preferably in a process that includes an oxidation of the D-amino acid. Preferably, the first catalyst is a biocatalyst that has at least, in part, a proteinaceous nature. More preferably, the biocatalyst is a protein, such as a substrate-specific enzyme. Most preferably, the first catalyst is an enantioselective amino acid oxidase. In the instant example, the first enantiomer is a D-amino acid and the enantioselective amino acid oxidase is a D-amino acid oxidase. Preferably, the D-amino acid oxidase is isolated from or having the amino acid sequence associated with *Trigonopsis variabilis*, *Rhodoturula gracilis*, or *Streptomyces ceolicolor*; more preferably, the D-amino acid oxidase used in the context of the present invention is isolated from *T. variabilis*.

A second example is essentially the converse of the first example, i.e., the stereoinversion of an L-amino acid into a D-amino acid, where all other aspects are the same. Accordingly, in the converse example, the first enantiomer is an L-amino acid and the enantioselective amino acid oxidase is an L-amino acid oxidase employed in the oxidation of the L-amino acid, which is part of the stereoinversion process that will ultimately result in an enrichment of D-amino acid. Alternative biocatalysts having the same or similar enantioselectivity set forth here and known to those skilled in the art are contemplated for use herein.

The oxidation reaction is preferably carried out in an aqueous phase within a bioreactor using an aliquot of the amino acid oxidase with substrate (i.e., the undesired amino acid enantiomer). Typically, substrate concentrations employed in the process are preferably between about 50 mM to about 2 M, though lesser and greater concentrations are contemplated herein. Reaction parameters such as pH, oxygen delivery, temperature, pressure, and mixing are preferably maintained at levels that favor optimal biocatalytic activity and stability, using standard methods known to those of ordinary skill in the art to determine such parameters.

The progress of this enantioselective oxidation reaction may be monitored in situ using analytical means well known in the art. In one embodiment, one or more oxygen sensors are associated with the bioreactor to enable monitoring of oxygen levels within the reaction system. In another embodiment, a dissolved oxygen monitor with a suitable detector or probe may be used to monitor the concentration of dissolved oxygen in the reaction medium as an indicator of reaction progression and completion. For example, a Mettler Toledo M700S with appropriate measuring module and dissolved oxygen probe (also a Mettler product) are usefully employed with the present invention. Verification of completion of the oxidation reaction may be carried out using HPLC analysis to determine the concentrations of keto acid and/or imine intermediate concentrations relative to the residual first amino acid enantiomer(s) concentration(s).

A byproducts of the biocatalytic oxidation reaction described above can arise from the decarboxylation of keto acid intermediates, an event mediated by $H_2O_2$ present within the reaction system and produced during the oxidase reaction. Therefore, the first step of the process of stereoinverting a first enantiomer into a second enantiomer preferably includes adding an inhibitor of decarboxylation of the intermediate. Formation of the aforementioned byproducts may affect the yield of the process and therefore one may prefer limiting the negative effects thereof. One approach to alleviate the effects of decarboxylation within the reaction system, includes the addition of a suitable inhibitor of decarboxylation (a reagent to remove $H_2O_2$), such as catalase. Preferably, the inhibitor is selected from the group consisting of a catalase, small keto acids, and metals and/or salts of metals known in the art. The further examples of inhibitors may be used separately or in conjunction with catalase. A preferred example of these reagents includes small keto acids. A suitable example of a small keto acid contemplated for use in the instant invention is pyruvic acid. Preferably, the inhibitor is in contact with a third surface associated with the reactor.

Catalase from a variety of microbial sources is commercially available (for example, from Sigma-Aldrich, St. Louis, Mo.), relatively inexpensive, and can be added in sufficient quantities to substantially or, preferably, completely eliminate decarboxylation of keto acid intermediates. As an alternative to commercial sources of catalase, a suitable microbial (or other organism) catalase can be prepared using methods similar to those discussed in the context of identifying, isolating, and expressing the amino acid oxidase biocatalysts above, such as, cloning of the catalase gene from its native host into a host readily employed for expression of an inserted gene, such as *E. coli*. using methods well known to those skilled in the art. Numerous microbial catalases that could be employed to retard or stop the aforementioned decarboxylation reaction are known in the art and can be identified as previously discussed. Examples of such catalases include those found in *E. coli, Aspergillus niger, Micrococcus luteus*, or *Geobacillus stearothermophilus*. In one embodiment, a gene encoding a suitable catalase may be cloned into a D- and/or an L-amino acid oxidase-expressing host such that the catalase and the D- and/or the L-amino acid oxidase may be coexpressed, and thus prepared in a single fermentation step and isolated together as a single ammonium sulfate preparation.

Upon completion of the oxidation reaction, the D-amino acid oxidase may be removed and/or deactivated using methods known to those skilled in the art, such as, for example, filtration, adsorption to solid supports such as Celite® (available from World Minerals, Santa Barbara, Calif.), and denaturation by known physical, chemical and/or enzymatic approaches. Preferably, the first catalyst, e.g., the amino acid oxidase, is in contact with a first surface; more preferably, the first catalyst is attached to the first surface such that it is immobilized thereon using approaches discussed above and others known in the art. When the amino acid oxidase is immobilized on the first surface, removal of the first surface from the site of reaction serves to remove the amino acid oxidase from the oxidation reaction system. The process of the present invention further preferably includes the second step of combining the intermediate with a second catalyst that is in contact with the second surface, a reductant, and an amine source, thereby resulting in the second (desired) enantiomer. The above discussion of the process as having a first step and a second step is made for purposes of illustrating one possible scenario in which the process may be applied. The first step and second step are chronologically interchangeable and no limitation as to which must occur first or second is contemplated herein globally, though, for a given starting material they may occur in a starting material-suitable order, as one example without limitation intended.

In this context, in one embodiment, the first step or the second step is carried out as a batch reaction, and thus neither the first step nor the second step need occur first, as would be the case in a continuous flow or saltatory process. Further, in another embodiment, the first step and the second step are carried out as a continuous process. When the first step and the second step are carried out as a continuous process, preferably, the continuous process is carried out at sites of reaction that are in serial fluid communication with each other. In any case, where the first step and the second step are carried out as batch reactions, continuous flow processes, or under other conditions, to achieve high yields and enantiomeric excesses, preferably, the process includes repeating the first step and the second step, in any order, as many times as are necessary to achieve the desired results.

As described above, the intermediate may include a keto acid and/or an imine. This step results in converting the intermediate into the second (desired) enantiomer. This second step that employs the second catalyst can take place in either the same site of reaction or one or more separate sites of reaction, such as a different vessel and/or a conduit, and the like. Suitable second catalysts preferably catalyze the reduction of the intermediate. In one embodiment, the reduction reaction is a reductive amination reaction of the intermediate. In this instance, the reductive amination reaction converts, for example, the keto acid into a racemic amino acid mixture that includes both desired and undesired enantiomers of an amino acid. In another embodiment, the reduction reaction converts an imine into desired and undesired enantiomers of an amino acid. The second catalyst, similar to the first catalyst may be a biocatalyst. Preferably, the second catalyst is an inorganic catalyst, more preferably, the second catalyst is a metal catalyst, more preferably the second catalyst is a metal included in but not limited to groups 8-12 of the Periodic Table, more preferably the second catalyst includes Pd, Pt, Ru, Rh, Ni, Cu, Zn, or Ir, more preferably, the second catalyst comprises Pd, Pt, and Ir, most preferably, the second catalyst comprises Pd. The second catalyst may be supported on a second surface such as, for example, carbon and/or alumina. In a preferred embodiment, the second surface comprises carbon, alumina, or Raney nickel, or is encapsulated in a polymeric layer. In a preferred embodiment, the second catalyst comprises Pd and the second surface comprises carbon. Additional second catalysts that may be usefully employed with the present invention include homogeneous metal hydride catalysts that are structurally similar to those described by Noyori (J. Am. Chem. Soc. 118:4916 (1996)), Ogo (J. Am. Chem. Soc. 126: 3020 (2004)), and Avecia (WO 98/42643, WO 00/18708, WO 01/12574, WO 02/44111)). Such catalysts are typically complexes of Rh, Ru, and Ir, although other metals may also be included.

Preferably, the metal catalysts are supported on structures that facilitate one-pot reactions, such as, for example, structures that may prevent contact of the biocatalyst and the metal catalyst through sequestration of the biocatalyst and/or the metal catalyst.

Many different types of commercially available supported metal catalysts can be used in the process of the present invention. Optimal metal catalysts can be chosen from those commercially available using small scale reactions that determine the relative performance of catalysts using parameters including but not limited to reaction rates, stability, substrate concentration and specificity, leaching of metal from the support, catalyst re-use, and tolerance of general reaction conditions. Catalyst selection can be assisted using statistical means to minimize the number of experiments required to determine the optimal catalyst and optimal catalyst usage for a given substrate. Computer software such as Design Expert (available from Stat-Ease Inc., Minneapolis, Minn.), among others, can be used to assist in the statistical design of experiments.

The first surface that is contemplated for the first catalyst (such as a biocatalyst) and the second surface that is contemplated for the second catalyst (such as a metal catalyst) include, for example, a structure through which a reaction solution may flow, including, for example, a membrane, a mesh, a tube, and the like, a structure that may serve a secondary purpose, such as, to stir the reaction solution, and a structure that may contain the reaction solution and/or facilitate transport of the reaction solutions from one reaction vessel to another. Such a structure includes a porous plate or other solid surface. When the first catalyst (e.g., a biocatalyst) and the second catalyst (e.g., a metal catalyst) are sequestered upon or within a structure that includes the first and/or second surface as described above, the sites of reaction and the reactions they catalyze occur upon or within the structure in question.

The reductant may be any suitable chemical donor including, but not limited to, hydrogen gas, a 5/2 ratio of formic acid/triethylamine, ammonium formate, $NaCNBH_3$, and amine-borane complexes. In a preferred embodiment, the reductant comprises hydrogen gas, or ammonium formate, or formic acid/triethylamine (5/2 ratio) mixture. A suitable buffer may be used to maintain the pH within the preferred range to maximize the yield and selectivity of the reductive amination reaction, such as those known in the art. Preferably, the amine source comprises ammonia or an ammonium salt. More preferably, ammonium formate is used as the amine source and further provides a convenient source of hydrogen, ammonia, as well as serving as the buffer for the reaction. Suitable concentrations of ammonium formate range from about 0.1 M to about 5 M, though lower and higher concentrations are suitable herein.

Further, in the process of the present invention that includes the first and second steps described above, preferably, the first catalyst and the second catalyst are prevented from contacting each other. With regard to the separation of the first catalyst from the second catalyst, one or both of the first catalyst and the second catalyst can be in solution in the same reaction vessel to the extent that one or both is compartmentalized. On the other hand, immobilization of the first or second catalyst on a surface, such as a reaction vessel wall or other structure can equally prevent the first catalyst from contacting the second catalyst. In either immediately preceding example, no cross-inhibiting activity of the first catalyst and the second catalyst should ensue.

In one embodiment, the first catalyst and the second catalyst are prevented from contacting each other because the reactor includes one or more sites of reaction. As described in detail above, the first catalyst and the second catalyst are preferably in contact with first and second surfaces, respectively, that serve to sequester each catalyst from the other. It is to be understood that the first and the second surfaces may be separate portions of a contiguous surface, which would allow a one-pot process, for example, where one site of reaction is employed that harbors both the first catalyst and the second catalyst. Therefore, in one embodiment, preferably, the first and second surfaces are included at or near the same site of reaction, i.e., within a single reactor vessel, but physically spaced apart.

Further, in the instant embodiment, preferably, the first surface or the second surface is removable from the site of reaction. Therefore, the first surface and the second surface are each contained on or in a structure that can be removed from the reactor, and thus, the structure is included at or one a site of reaction. In another embodiment, the structure is part of the site of reaction, for example, when the structure is a catalyst basket, or conversely, the structure is removable from the site of reaction. The ability to remove the first surface or the second surface from the site of reaction allows for the use of a single reaction vessel to be employed without the need for transferring the reaction solution. This use of a single reaction vessel is due to the ability to simply change the reaction conditions within the single reaction vessel to suit a one or another catalyst. This approach allows for maximizing the efficiency of each reaction without compromising the other. Along the same lines, preferably, the first surface and the second surface are removable from the site of reaction. The ability to remove both surfaces from the site of reaction enables additional manipulations of the reaction solution without risking harm to either the first catalyst or the second catalyst and therefore may enable one or both catalysts, when the first catalyst and/or the second catalyst is reusable, to be reused in subsequent reactions with the same reaction solution, for example, or with new reaction solutions. Further, this allows for a preferred embodiment, wherein the first catalyst of the second catalyst, but not both catalysts, is included at the same site of reaction at the same time.

When the reactor includes more than one site of reaction, preferably, multiple site of reactions are employed. In this context, multiple structures having the first catalyst only may be included within the reactor. Such an arrangement further enables regulation of at least the reaction size through allowing very precise control of the amount of the first catalyst present in the reactor through increasing or decreasing the number of site of reactions and correspondingly varying the amount of catalyst present in the reactor.

On the other hand, the optimal reaction conditions for one catalyst, be it the first or second, are likely detrimental to the other, as is often the case with conditions such as temperature, pH, pressure, and the like. Therefore, removing the first catalyst from the site of reaction where the second catalyst is to be employed is preferred. When the process includes more than one site of reaction, independent optimization of the reductive amination and biocatalytic oxidation reactions is facilitated. In one embodiment, the reductive amination step is carried out at a temperature of about 30° C. to about 200° C. Preferably, the temperature is about 50° C. to about 200° C., and more preferably, the temperature is about 50° C. to about 150° C., and yet more preferably, the temperature is about 65° C. to about 100° C. Further, the reductive amination step may be carried out over a pH range of about 4 or lower to about 12 or greater; indeed, the reduction amination step may be accomplished at a pH between about 3 to about 14. Preferably, the reductive amination step is carried out at a pH of about 4 to about 12; more preferably, the reductive amination step is carried out at a pH of about 6 to about 12; and yet more preferably, the reductive amination step is carried out at a pH of about 8 to about 12. The reductive amination step is also pressure sensitive and preferably is carried out at a pressure of about 5 psi to about 3000 psi; more preferably, this step is carried out at a pressure of about 50 psi to about 250 psi.

The concentration of metal catalyst necessary to provide effective catalysis of the reaction will depend upon the particular catalyst chosen and preferably is in the range of about 0.01 mol % to about 3 mol %. In a preferred embodiment, a catalyst system includes a catalyst composition of 5% Pd on carbon at a reaction composition of about 0.01 mol % to about 5 mol % with about 500 mM to about 5 M ammonium formate. In an especially preferred embodiment of the process, the same Pd on carbon catalyst is used in a pressure reactor using hydrogen gas and ammonia at a pressure in the range of about 50 psi to about 250 psi at a temperature between about 50° C. and 200° C.

The completion of the reductive amination reaction is determined by analysis of reaction samples using HPLC analysis or by cessation of hydrogen uptake or by cessation of gassing. A reaction byproducts comprising a dimer, arising from the reduction of the condensation product of amino acid and keto acid, can occur in the reductive amination. An additional by-product can be formed by the direct reduction of the keto acid to the 2-hydroxy acid. Both impurities may be suppressed by addition of excess ammonia or ammonium salt to the reaction, which has no adverse effect upon productivity. Excess ammonia can be added as ammonia, ammonium formate, and/or an ammonium salt including, but not limited to ammonium chloride. The reaction is allowed to proceed until the residual ammonium formate has been consumed by reaction with the metal catalyst and has consequently been vented from the reaction as carbon dioxide and/or hydrogen gas. Upon completion of the reaction, the supported metal catalyst can be removed from the reaction and recovered by mechanical means including, but not limited to, filtration, adsorption to solid materials, or when compartmentalized using a catalyst basket or other catalyst enclosure may simply be removed by removing the catalyst compartment. Following removal of the metal catalyst, residual salts such as chloride ion can be removed by chromatographic means such as ion-exchange chromatography or by electrodialysis or crystallization.

An advantage of the current process over earlier deracemization processes using supported metal catalysts is that the recovered metal catalyst is not deactivated and can be reused in further reactions or reprocessed by the catalyst manufacturer to recover and recycle the precious metal. Further, by immobilizing all biocatalysts (e.g., amino acid oxidases and catalases) and the metal catalyst, they are prevented from contacting and fouling each other. Therefore, all catalysts used in the process may have some degree of reusability.

The reaction medium containing racemic amino acid is now enriched and may be further enriched in the desired amino acid enantiomer by sequential oxidation and reductive amination reactions. The reaction medium can be subjected to additional cycles of oxidation and reduction until the optimal yield of the desired amino acid enantiomer is obtained. Once the optimal yield has been selected, based upon productivity and cost parameters, the process is completed by ending the sequential oxidation and reduction reactions. The final step is preferably an oxidation step to convert any remaining quantity of the undesired enantiomer of the amino acid to its corresponding keto acid. The final oxidation reaction ensures that enantiopure amino acid product is obtained.

The theoretical maximum yield of optically pure enantiomer is 100%. The oxidation and reductive amination reactions can be carried out in a wide range of reactor vessels including, but not limited to a stirred tank reactor, fermentation vessels, hollow fiber membrane bioreactors, oscillatory baffled reactors and/or a counter current chromatographic reactor. The oxidation and reductive amination reaction processes can be operated as batch oxidation and reductive amination reactions or as a continuous process using independent but serially fluidly linked oxidation and reductive amination reactor vessels. In a preferred embodiment, the biocatalytic oxidation reaction is carried out in a membrane bioreactor, and the reductive amination reaction is carried out in a stirred tank reactor or a fixed bed reactor or a continuous stirred tank reactor. The use of a membrane bioreactor offers the advantage of simplified and highly economical biocatalyst retention, recovery and re-use. In a preferred embodiment, batch reactors are employed for both the oxidation step and the reduction amination step. In another preferred embodiment, a membrane reactor is used for the oxidation step. Overall, the most preferred embodiment includes use of a reactor for the reduction step where the reactor can withstand pressures of up to at least 250 psi and temperatures up to about 200° C. An example of a preferred reactor is a fixed bed reactor, as is known in the art.

The following examples set forth representative illustrations of certain preferred embodiments of the invention. No limitation of the invention as claimed should be inferred from these examples as none is implied. Chemicals set forth in the examples that are used for stock solutions and growth media are readily available from commercial sources, such as, for example, Sigma-Aldrich, Inc. (St. Louis, Mo.). All chemicals used are reagent grade.

Example 1

The following example illustrates one method for the preparation of an amino acid oxidase.

A recombinant *Escherichia coli* containing D-amino acid oxidase from *Trigonopsis variabilis* was constructed using standard methods as set forth by Alonso et al., Enzyme and Microbial Technology 25:88-95 (1999). The recombinant *E. coli* strain is referred to herein as *E. coli*$^{Tv\text{-}DAO}$.

Suitable growth media ("GM") are prepared from sterile stock solutions, as follows. A stock salts solution ("Salts Stock") is prepared by combining appropriate amounts of various salts and water such that the following salt concentrations are obtained: 10 g/L $(NH_4)_2SO_4$, 73 g/L $K_2HPO_4$, 18 g/L $NaH_2PO_4.2H_2O$, and 2.5 g/L $(NH_4)_2H$-Citrate; the solution is mixed and autoclaved. A stock trace elements solution ("Trace Elements Stock") is prepared by combining appropriate amounts of various salts and water such that the following salt concentrations are obtained: 0.5 g/L $CaCl_2.2H_2O$, 10.03 g/L $FeCl_3$, 0.18 g/L $ZnSO_4.7H_2O$, 0.16 g/L $CuSO_4.5H_2O$, 0.15 g/L $MnSO_4.H_2O$, 0.18 g/L $CoCl_2.6H_2O$, and 22.3 g/L $Na_2EDTA.2H_2O$; the solution is mixed and autoclaved. To prepare 200 ml of GM, the following components are combined in a 1 L culture flask: 40 ml of Salts Stock; 0.4 ml of Trace Elements Stock; 0.4 ml of a sterile solution of 1 M $MgSO_4.7H_2O$; 2 ml of a sterile 50% glucose solution; a suitable antibiotic corresponding to the antibiotic resistance marker of the plasmid vector which carries the DAO gene, typically chloramphenicol at 10 mg/ml, kanamycin at 40 mg/ml, or ampicillin at 100 mg/ml, and sterile water to 200 ml total volume.

The culture flask is inoculated with an aliquot, typically 0.5 ml, of *E. coli*$^{Tv\text{-}DAAO}$. The culture is incubated at 30° C. or 37° C. with agitation until an optical density ($OD_{600}$) of 0.6 is reached. Thereafter, expression of the amino acid oxidase gene is induced using a suitable inducer which corresponds to the expression system used on the plasmid vector, for example 1 mm IPTG, 0.2% arabinose, or a 30 min temperature shift to 42° C. The culture is incubated for a further 4-8 hrs at 30° C. or 37° C. following the addition of inducer to allow enzyme induction to reach maximal levels. Following induction, cells are recovered by centrifugation at 5,000 g for 30 min. The resulting cell pellets are stored at −20° C.

Example 2

This example illustrates one method for ammonium sulfate fractionation of the amino acid oxidase from bacterial cultures.

Cells prepared in accordance with the protocol of Example 1, or other suitable protocols as are known in the art, were lysed using a French Pressure Cell, pelleted at 10,000 g for 30 min at 4° C., and the pellet discarded, leaving a first supernatant. Solid ammonium sulfate was added gradually to the first supernatant and mixed until the first supernatant reached a final concentration of 30% saturated (100% ammonium sulfate saturation at 25° C. is 541 g/L and at 0° C. is 514 g/L) corresponding to a final ammonium sulfate concentration of approximately 160 g/L (±5 g/L). The first supernatant was then centrifuged as before and the resultant pellet was discarded, leaving a second supernatant. Solid ammonium sulfate was then added gradually to the second supernatant and mixed until the second supernatant reached a final concentration of 60% saturated corresponding to a final ammonium sulfate concentration of 312 g/L (±5 g/L). The second supernatant was centrifuged as before, the resulting pellet was retained, and the third supernatant was discarded. The retained pellet from the final centrifugation was an ammonium sulfate fraction enriched in amino acid oxidase, which was stored at 4° C. The isolated biocatalyst was utilized in subsequent examples.

Example 3

The following example is illustrative of one method of the reductive amination reaction of 2-ketobutyrate.

Ammonium formate (1.89 g, 0.03 mol) was added to 25 ml of water in a 1 L round-bottomed reaction flask that was connected to a standard reflux condenser. A palladium-carbon catalyst (5% Pd on carbon, Degussa type E101 O/W, 10.6 g, 2.5 mmol, 0.5 mol % relative to 2-ketobutyric acid) was added to the flask, and the solution was heated to 90-100° C. while stirring, using a standard stirring, heating mantle.

In a separate conical flask, 25.5 g (0.25 mol) of 2-ketobutyric acid and 39.4 g (0.625 mol) of ammonium formate were dissolved in 250 ml water. The resultant keto acid/formate solution was added slowly over a period of one to two hrs to the reaction flask (2-4 ml/min) using a peristaltic pump or dropping funnel. The reaction was incubated for an additional 30 minutes and sampled regularly for HPLC analysis using standard techniques to determine conversion of 2-ketobutyrate. Upon reaching a >98% 2-ketobutyrate conversion, the reaction is allowed to cool. The Pd/C catalyst was removed by filtration and retained for subsequent batches. The final concentration of DL-2-aminobutyric acid was determined by HPLC analysis of the filtrate using standard techniques. The yield of DL-2-aminobutyric acid exceeded 98%. The DL-2-aminobutyric acid product was recovered by concentration and filtration and used directly in a subsequent oxidation reaction.

Example 4

The following example is illustrative of one method for the oxidation of D-2-aminobutyric acid in a racemic mixture of DL-2-aminobutyric acid.

In a 1 L beaker, 51.5 g (0.5 mol) of DL-2-aminobutyric acid were added to 250 ml of water, and the pH adjusted to 7.5-8.0 using concentrated $NH_4OH$ and concentrated HCl if necessary. The mixture was transferred to a jacketed vessel and maintained at 25° C. One milliliter of 50% aqueous polypropylene glycol (Sigma-Aldrich, St. Louis Mo.) was added to the vessel, and the mixture was agitated at 600 rpm. The mixture was sparged with $O_2$ via a metal frit at a flow rate of 0.25-0.5 L/min ensuring that the gas stream was dispersed efficiently. Dissolved oxygen in the mixture was monitored using a calibrated oxygen electrode (Mettler Toledo, M700S, Mettler-Toledo, Inc., 1900 Polaris Parkway, Columbus, Ohio). The dissolved oxygen concentration was recorded, typically the concentration of dissolved oxygen was between 33-40 mg/L prior to the addition of enzymes. Two milliliters of Catazyme® (catalase from *Aspergillus niger*, purchased from Novozymes) were preheated to 50° C. for 5 min and then added to the mixture. D-amino acid oxidase (2.5 g, 1250 units) was added to the mixture. Additional Catazyme® (1 ml, similarly preheated) was added to the reaction at hourly intervals following the addition of the D-amino acid oxidase. When the $DO_2$ returns to the initial reading, a sample was taken to determine the enantiomeric excess ("e.e.") of L-2-aminobutyric acid by HPLC. When the e.e. of L-2-aminobutyric acid was demonstrated to be >99%, the solution was decanted into a 2 L beaker. The final concentration of 2-ketobutyric acid product was determined by HPLC and shown to have been formed in >95% yield. The enzymes in the solution were removed by heating the solution to 90° C., adding Celite® (World Minerals Inc.), and then filtering through a sintered glass funnel. The filtrate of the reaction was used directly in the subsequent reduction step.

Example 5

The following example illustrates one method for the reductive amination of 2-ketobutyrate from a bio-oxidation reaction.

Ammonium formate (1.89 g, 0.03 mol) and 10.6 g (2.5 mmol, 0.5 mol % relative to 2-ketobutyric acid) of 5% Pd on carbon (Pd/C) were added to 25 ml of water in a 1 L round-bottomed reaction flask connected to a reflux condenser. The mixture was heated to 90-100° C. using a stirring, heating mantle. In a separate conical flask, 39.4 g (0.625 mol) of ammonium formate were added to the filtrate from the bio-oxidation reaction (see Example 4). This mixture was added slowly over a period of one to two hrs to the reaction flask (2-4 ml/min), as described above. The reaction mixture was incubated for an additional 30 min and sampled regularly for HPLC analysis using standard techniques to determine conversion of 2-ketobutyrate. When 2-ketobutyrate conversion reached >98%, the reaction was allowed to cool. The Pd/C catalyst was removed by filtration and retained for subsequent batches. The yield of DL-2-aminobutyric acid was found to have exceeded 98%.

The final concentration of non-racemic 2-aminobutyric acid product was determined by HPLC analysis of the filtrate. Further, the 2-aminobutyric acid product was recovered by concentration and filtration, and/or the solution was used directly in subsequent oxidation reactions.

Example 6

The following example illustrates one method for the oxidation of D-2-aminobutyric acid in a racemic mixture of DL-2-aminobutyric acid.

The pH of the reductive amination filtrate of 2-ketobutyrate from Example 5 was adjusted to 7.5-8.0 using concentrated HCl. The solution was transferred to a jacketed vessel and maintained at 25° C. One milliliter of polypropylene glycol was added, and the mixture was agitated at 600 rpm. The mixture was sparged with $O_2$ via a metal frit at a flow rate of 1 L/min to ensure that the gas stream was dispersed efficiently. Dissolved oxygen in the mixture was monitored using a calibrated oxygen electrode (Mettler Toledo, M700S). The dissolved oxygen concentration was recorded, typically the concentration of dissolved oxygen was between 33-40 mg/L prior to the addition of enzymes. D-amino acid oxidase (2.5 g, 675 units) was added to the mixture. When the $DO_2$ returned to the initial reading, a sample was taken to determine the e.e. of L-2-aminobutyric acid by HPLC analysis. When the e.e. of L-2-aminobutyric acid was demonstrated to be >99%, the mixture was decanted into a 2 L beaker. The enzymes in the solution were heat-inactivated at 90° C. and removed therefrom by adding activated charcoal and filtering though a sintered glass funnel. L-aminobutyric acid was isolated by concentration of the solution and crystallization of the product and was recovered in 69% yield based on the racemic 2-aminobutyric acid charged in Example 4. The maximum theoretical yield from this cycle is 75%. Alternately, the filtrate of the reaction could be used directly in a subsequent reduction step.

Example 7

The following example illustrates oxidation of D-norvaline in a racemic mixture of DL-norvaline using the an embodiment of the present invention.

Thirty grams (0.256 mol) of DL-norvaline were added to 300 ml of water in a 1 L beaker. The solution was warmed with stirring to dissolve the amino acid and the pH adjusted to 7.5-8.0. The solution was transferred to a jacketed vessel and maintained at 25° C. One milliliter of polypropylene glycol (Sigma-Aldrich) was added, and the solution was agitated at 600 rpm. Oxygen gas was sparged via a metal frit at a flow rate 1 L/min to ensure gas stream was beneath the stirrer to disperse bubbles efficiently. The dissolved oxygen in the mixture was monitored using a calibrated oxygen electrode, as described above. Two milliliters of Catazyme (Novozymes)

were preheated to 50° C. for 5 min and added to the mixture. Two and a half grams of D-amino acid oxidase (1250 units were then added to the mixture. An additional 1 ml of Catazyme (similarly preheated) was added to the reaction hourly following addition of the D-amino acid oxidase. When the $DO_2$ returned to the initial reading, a sample was taken to determine the e.e. of L-2-norvaline by HPLC analysis. When the e.e. of L-2-norvaline was demonstrated to be >99%, the solution was decanted into a 2 L beaker. The final concentration of 2-oxovaleric acid product was determined by HPLC analysis to have a yield >98%. The enzymes in the solution were removed by heating the solution to 90° C. and adding Celite® before filtering though a sintered glass funnel. The filtrate of the reaction was used directly in a subsequent reduction step.

Example 8

The following example illustrates one method for oxidizing D-tert-leucine in a racemic mixture of DL-tert-leucine.

In a 1 L beaker, 3.3 g of DL-tert-butylglycine (0.025 mol) was dissolved into 300 ml of water and the pH adjusted to 7.5-8.0 using concentrated $NH_4OH$. The solution was transferred to a jacketed vessel and maintained at 25° C. Polypropylene glycol (1 ml) was added, and the mixture was agitated at 600 rpm. Oxygen gas was sparged via a metal frit at a flow rate of 1 L/min. The dissolved oxygen in the mixture was monitored using a calibrated oxygen electrode described in previous examples. Two milliliters of Catazyme (Novozymes) were preheated to 50° C. for 5 min and added to the mixture. Twenty grams of D-amino acid oxidase (500 units) were added to the mixture. An additional 1 ml of Catazyme (similarly preheated) was added to the reaction hourly following D-amino acid oxidase addition. When the $DO_2$ returned to the initial reading, a sample was taken to determine the e.e. of L-tert-butylglycine by HPLC analysis. When the e.e. of L-tert-butylglycine was demonstrated to be >99%, the solution was decanted into a 2 L beaker. The final concentrations of trimethylpyruvate and residual L-tert-butylglycine were determined by HPLC analysis. The enzymes in the solution were removed by heating the solution to 90° C. and adding Celite® before filtering through a sintered glass funnel. The filtrate of the reaction was used directly in a subsequent reduction step, and L-tert-butylglycine was isolated by concentration and crystallization using standard methods.

Example 9

This example illustrates a method for the reductive amination of trimethyl pyruvic acid in accordance with the present invention.

In a 100 ml hydrogenation vessel (Parr reactor), 6.75 ml of 60% (v/v in water) trimethyl pyruvic acid, 7.10 ml of 35% ammonium hydroxide, and 17.15 ml of water were combined. To this mixture, 1.25 g of 5% Pd/C was added. The hydrogenation apparatus (100 ml Parr autoclave, Parr Instrument Company, Moline, Ill.) was set up with stirring, the hydrogen pressure set-point was 200 psi, and temperature set-point was 50° C. The reaction was stirred under these conditions for 4 hrs. The contents of the vessel were then filtered through a glass sintered funnel, and the filtrate containing DL-tertbutylglycine product was collected.

Example 10

This example illustrates one reactor system that may be usefully employed in the present invention.

Referring to FIG. 1, one reactor configuration for the process described herein is illustrated at 10. The process can start at various points including the reaction/feed vessel 12 or the hold tank 14 and cycle one or more times. Starting from the reaction feed vessel 12, the following steps occur: 1) substrate, for example, an enantiomer, a first catalyst, for example, an amino acid oxidase biocatalyst, and oxygen are combined in the reaction feed vessel. This mixture begins to react and is pumped through the membrane filter/reactor 16. From this point, the reaction mixture can cycle back through the feed vessel 12 and again through the membrane filter/reactor 16. Small molecules (<30 k M.W.), but not the amino acid oxidase biocatalyst, can pass through the membrane 18 to form permeate 20, which is passed to the hold tank 14. The ratio of permeate 24 to reaction mixture, which returns to the feed vessel 12 is controlled by a valve 22 in the permeate line 24. The valve 22 is adjusted to allow the appropriate retention time for maximal oxidation of substrate to product. The permeate 20 from the membrane reaction is degassed of residual oxygen and is then pumped from the hold tank 14 to the high pressure column reactor 26, where reductive animation of keto acid to racemic amino acid occurs. Prior to entering the high pressure column reactor 26, the permeate 20 is mixed with hydrogen and ammonia gases through a mixing valve 28. In the high pressure column reactor 26, reductive amination occurs under pressure to drive the reaction to completion. The pressure is controlled by column back pressure or an additional restriction plate (not shown) to increase pressure further to achieve optimal reaction conditions. The output from the high pressure column reactor 26 enters a degassing tank 30 where residual hydrogen and ammonia gases are removed, and the mixture is then returned to the feed vessel 12 to begin another cycle. An appropriate number of cycles are carried out until the desired yield and enantiomeric excess of product is achieved.

Obvious variations and modifications of this invention are contemplated as part hereof and will be apparent to those skilled in the art. This invention is not limited except as set forth in the following claims.

What is claimed:

1. A process to stereoinvert a first enantiomer into a second enantiomer in a single reactor that includes a first surface and a second surface, comprising the steps of:
    a) combining the first enantiomer, oxygen, and a first catalyst that is in contact with the first surface, thereby resulting in an intermediate; and
    b) combining the intermediate, a second catalyst that is in contact with the second surface, a reductant, and an amine source, thereby resulting in the second enantiomer;
    wherein the first surface and the second surface are different and the first catalyst and the second catalyst are prevented from contacting each other.

2. The process of claim 1, wherein the first surface or the second surface is removable from the reactor.

3. The process of claim 1, wherein the oxidation product is an imine intermediate or a keto acid.

4. The process of claim 1, wherein the first catalyst is an enantioselective amino acid oxidase.

5. The process of claim 4, wherein the first enantiomer is a D-amino acid and the enantioselective amino acid oxidase is a D-amino acid oxidase.

6. The process of claim 4, wherein the first enantiomer is an L-amino acid and the enantioselective amino acid oxidase is an L-amino acid oxidase.

7. The process of claim 1, further comprising preventing decarboxylation of the keto acid during the oxidizing step.

8. The process of claim 7, wherein the preventing step takes place in the presence of a catalase.

9. The process of claim 8, wherein the catalase is attached to a removable surface.

10. The process of claim 1, wherein the second catalyst comprises palladium, platinum, ruthenium, rhodium, nickel, copper, zinc, or iridium.

11. The process of claim 10, wherein the second catalyst is deposited on a surface comprising carbon, alumina, or Raney nickel.

12. The process of claim 1, wherein the reductant comprises hydrogen gas or ammonium formate.

13. The process of claim 1, wherein the reactor includes multiple reaction chambers.

14. The process of claim 1, wherein the reactor comprises one of the group consisting of a stirred tank reactor, a fermentation vessel, a hollow fiber membrane bioreactor, an oscillatory baffled reactor, and a counter current chromatographic reactor.

15. The process of claim 14, wherein the oxidizing step and the reducing step are carried out as a continuous process.

16. A process to stereoinvert a first enantiomer into a second enantiomer in a single reactor, comprising the steps of:
   a) combining the first enantiomer, oxygen, and a first catalyst, thereby resulting in an intermediate; and
   b) combining the intermediate, a second catalyst, a reductant, and an amine source thereby resulting in the second enantiomer;
   wherein step (a) and step (b) take place at different times.

17. A process to stereoinvert a first enantiomer into a second enantiomer in a single reactor that includes a first surface and a second surface, comprising the steps of:
   a) combining the first enantiomer, oxygen, and a first catalyst that is in contact with the first surface, thereby resulting in an intermediate; and
   b) combining the intermediate, a second catalyst that is in contact with the second surface, a reductant, and an amine source, thereby resulting in the second enantiomer;
   wherein the first surface and the second surface are different and step (a) or step (b) is performed first; step (a) is complete before step (b) begins; and step (a) and step (b) are performed at or near different sites within the reactor.

18. The process of claim 17, wherein the first surface or the second surface is removable from the reactor.

19. The process of claim 17, further comprising preventing decarboxylation of the intermediate during the oxidizing step.

20. A process to stereoinvert a first enantiomer into a second enantiomer in a single reactor that includes a first surface and a second surface, comprising the steps of:
   a) combining the first enantiomer, oxygen, and a first catalyst that is in contact with the first surface, thereby resulting in at least one of a keto acid intermediate or an imine intermediate; and
   b) combining the at least one of a keto acid intermediate or an imine intermediate, a second catalyst that is in contact with the second surface, a reductant, and an amine source, thereby resulting in the second enantiomer;
   wherein the first surface and the second surface are different and the first catalyst and the second catalyst are prevented from contacting each other; the first catalyst is an enantioselective amino acid oxidase that is specific for at least one of a D-amino acid or an L-amino acid; the second catalyst is a metal catalyst that includes palladium on carbon; the reductant includes hydrogen gas; and the amine source comprises ammonia or an ammonium salt.

21. A process to stereoinvert a first enantiomer into a second enantiomer in a reactor that includes a first surface and a second surface, comprising the steps of:
   a) combining the first enantiomer, oxygen, and a first catalyst that is in contact with the first surface, thereby resulting in an intermediate; and
   b) combining the intermediate, a second catalyst that is in contact with the second surface, a reductant, and an amine source, thereby resulting in the second enantiomer;
   wherein the first catalyst and the second catalyst are prevented from contacting each other; and the first surface or the second surface is removable from the reactor.

22. A process to stereoinvert a first enantiomer into a second enantiomer in a reactor that includes a first surface and a second surface, comprising the steps of:
   a1) combining the first enantiomer, oxygen, and a first catalyst that is in contact with the first surface, thereby resulting in an intermediate keto acid;
   a2) preventing decarboxylation of the keto acid during the oxidizing step; and
   b) combining the intermediate keto acid, a second catalyst that is in contact with the second surface, a reductant, and an amine source, thereby resulting in the second enantiomer;
   wherein the first catalyst and the second catalyst are prevented from contacting each other;
   the preventing step takes place in the presence of a catalase; and the catalase is attached to a removable surface.

23. A process to stereoinvert a first enantiomer into a second enantiomer in a reactor that includes a first surface and a second surface, comprising the steps of:
   a) combining the first enantiomer, oxygen, and a first catalyst that is in contact with the first surface, thereby resulting in an intermediate; and
   b) combining the intermediate, a second catalyst that is in contact with the second surface, a reductant, and an amine source, thereby resulting in the second enantiomer;
   wherein the first catalyst and the second catalyst are prevented from contacting each other; the reactor comprises one of the group consisting of a stirred tank reactor, a fermentation vessel, a hollow fiber membrane bioreactor, an oscillatory baffled reactor, and a counter current chromatographic reactor; and the oxidizing step and the reducing step are carried out as a continuous process.

24. A process to stereoinvert a first enantiomer into a second enantiomer in a reactor that includes a first surface and a second surface, comprising the steps of:
   a) combining the first enantiomer, oxygen, and a first catalyst that is in contact with the first surface, thereby resulting in an intermediate; and
   b) combining the intermediate, a second catalyst that is in contact with the second surface, a reductant, and an amine source, thereby resulting in the second enantiomer;
   wherein step (a) or step (b) is performed first; step (a) is complete before step (b) begins; and step (a) and step (b) are performed at or near different sites within the reactor; and the first surface or the second surface is removable from the reactor.

* * * * *